(12) United States Patent
Aoki

(10) Patent No.: US 7,568,477 B2
(45) Date of Patent: Aug. 4, 2009

(54) CONTROL SYSTEM FOR AN EXHAUST GAS SENSOR

(75) Inventor: Keiichiro Aoki, Susono (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 336 days.

(21) Appl. No.: 10/574,925

(22) PCT Filed: Dec. 9, 2004

(86) PCT No.: PCT/JP2004/018769

§ 371 (c)(1), (2), (4) Date: Apr. 7, 2006

(87) PCT Pub. No.: WO2005/071247

PCT Pub. Date: Aug. 4, 2005

(65) Prior Publication Data

US 2007/0125348 A1    Jun. 7, 2007

(30) Foreign Application Priority Data

Jan. 23, 2004    (JP)    ............................. 2004-015759

(51) Int. Cl.
*F02D 41/00*    (2006.01)
(52) U.S. Cl. .................... 123/676; 219/494
(58) Field of Classification Search ............... 123/676, 123/677, 678, 689, 697; 219/491, 494, 205; 204/424, 425, 431, 432
See application file for complete search history.

(56) References Cited

U.S. PATENT DOCUMENTS

| | | | |
|---|---|---|---|
| 3,946,198 A | 3/1976 | Foote | |
| 4,055,792 A | 10/1977 | Foote | |
| 4,655,182 A | 4/1987 | Nakano et al. | |
| 4,753,204 A | 6/1988 | Kojima et al. | |
| 4,765,298 A | 8/1988 | Kojima et al. | |
| 4,915,082 A | 4/1990 | Uchinami et al. | |
| 5,101,625 A | 4/1992 | Sugino et al. | |
| 5,492,107 A | 2/1996 | Furuya | |
| 5,606,855 A | 3/1997 | Tomisawa | |
| 5,616,835 A | 4/1997 | Schnaibel et al. | |
| 5,740,675 A | 4/1998 | Shimasaki et al. | |

(Continued)

FOREIGN PATENT DOCUMENTS

DE    43 00 530 A1    7/1994

(Continued)

*Primary Examiner*—Stephen K Cronin
*Assistant Examiner*—Arnold Castro
(74) *Attorney, Agent, or Firm*—Oliff & Berridge, PLC

(57) ABSTRACT

An oxygen sensor is mounted in an exhaust path of an internal combustion engine. The status of an exhaust gas is detected in accordance with the output of the oxygen sensor. The oxygen sensor incorporates a heater for heating an element of the sensor. In a region in which the temperature of the sensor element is below 300° C., an adsorbable species becomes adsorbed. In a region in which the exhaust pipe temperature is above 80° C., the adsorbable species becomes adsorbed remarkably. Power supply control is continuously exercised over the heater so as to maintain the sensor element at a temperature of 300° C. or higher until the exhaust pipe temperature drops below 80° C. after an internal combustion engine stop. The power supply to the heater is shut off after the exhaust pipe temperature drops below 80° C.

3 Claims, 10 Drawing Sheets

U.S. PATENT DOCUMENTS

| | | |
|---|---|---|
| 6,304,813 B1 | 10/2001 | Ikeda et al. |
| 6,305,348 B1 | 10/2001 | Grosmougin et al. |
| 6,543,431 B2 * | 4/2003 | Surnilla et al. .............. 123/685 |
| 2003/0029426 A1 | 2/2003 | Surnilla et al. |
| 2003/0213795 A1 | 11/2003 | Toyoda |

FOREIGN PATENT DOCUMENTS

| | | |
|---|---|---|
| DE | 100 15 282 A1 | 11/2000 |
| JP | EP 0 262 956 A1 | 4/1988 |
| JP | A 1-257739 | 10/1989 |
| JP | A 4-359142 | 12/1992 |
| JP | U 6-58359 | 8/1994 |
| JP | A 8-75695 | 3/1996 |
| JP | A 2000-097902 | 4/2000 |

* cited by examiner

FIG. 6

THTSP MAP FOR GAsum

| GAsum[g/S] | 3000 | 10000 | 50000 |
|---|---|---|---|
| THTSP[COUNT] | 10000 | 30000 | 80000 |

KOXSRI MAP FOR TENGSP

| TENGSP [s] | 3000 | 10000 | 50000 |
|---|---|---|---|
| KOXSRI [V] | 0.0 | 0.1 | 0.2 |

KOXSRM MAP FOR TENGSP

| T300 [s] | 30 | 100 | 180 |
|---|---|---|---|
| KOXSRM [V] | 0.0 | 0.1 | 0.2 |

CONTROL SYSTEM FOR AN EXHAUST GAS SENSOR

TECHNICAL FIELD

The present invention relates to an exhaust sensor controller, and more particularly to an exhaust sensor controller for controlling the status of an exhaust sensor that is mounted in an exhaust path to detect the status of an internal combustion engine exhaust gas.

BACKGROUND ART

In a conventionally known system disclosed, for instance, by Japanese Patent Laid-open No. Hei 4-359142, an oxygen sensor is mounted in an internal combustion engine exhaust path to detect the status of an exhaust gas. The oxygen sensor generates an output in accordance with the oxygen concentration in the exhaust gas after reaching its activity temperature. To this end, the oxygen sensor incorporates a heater, and heated to its activity temperature by the heater while the internal combustion engine is operating.

The exhaust gas contains a large amount of water vapor. Therefore, if the oxygen sensor temperature suddenly drops after an internal combustion engine stop, a large amount of water is adsorbed by a sensor element of the oxygen sensor. This water adsorption may give a thermal shock to the sensor element, thereby damaging the sensor element. Therefore, the above-mentioned conventional system continuously heats the oxygen sensor for a period of approximately 5 seconds after an internal combustion engine stop.

When the oxygen sensor is continuously heated for a period of approximately 5 seconds after an internal combustion engine stop, the sensor temperature does not suddenly drop. As a result, the proportion of water remaining in the exhaust path that is adsorbed by the sensor element significantly decreases. As such being the case, the above-mentioned conventional system can improve the durability of the oxygen sensor by restraining the adsorption of water by the oxygen sensor at the time of an internal combustion engine stop.

Including the above-mentioned document, the applicant is aware of the following documents as a related art of the present invention.

[Patent Document 1]
Japanese Patent Laid-open No. Hei 4-359142
[Patent Document 2]
Japanese Patent Laid-open No. Hei 8-75695
[Patent Document 3]
Japanese Utility model Laid-open No. Hei 6-58359
[Patent Document 4]
Japanese Patent Laid-open No. Hei 1-257739

After internal combustion engine startup, the internal combustion engine exhaust sensor is generally heated to a predetermined activity temperature. In such a heating process, the output from the exhaust sensor temporarily deviates from normal due to the influence of adsorbable species on the sensor element. It is assumed that the adsorbable species becomes chemically adsorbed to the sensor element when the exhaust sensor temperature lowers after an internal combustion engine stop. The deviation of the exhaust sensor output due to the influence of the adsorbable species increases with an increase in the amount of adsorbable species adsorption.

The applicant of the present invention has found that the amount of adsorbable species adsorption to the exhaust sensor greatly depends on the exhaust sensor temperature and ambient temperature prevailing after an internal combustion engine stop. More specifically, it is found that if the exhaust sensor temperature lowers to reach a temperature region in which the adsorbable species may become chemically adsorbed (hereinafter referred to as the "absorption temperature region") before the exhaust path temperature sufficiently lowers, a large amount of adsorbable species readily becomes adsorbed.

According to the system disclosed by Japanese Patent Laid-open No. Hei 4-359142, the oxygen sensor is continuously heated for a period of approximately 5 seconds after an internal combustion engine stop. That is, the system has a function for delaying the temperature of the exhaust sensor (oxygen sensor) lowering into the adsorption temperature region while the process for lowering the exhaust path temperature is in progress.

However, the above-mentioned conventional system stops to heat the oxygen sensor before the exhaust path temperature sufficiently lowers. More specifically, the exhaust path temperature does not significantly lower during the 5 second in which the above conventional system continuously heats the oxygen sensor. Therefore, the above conventional system cannot decrease the amount of adsorbable species adsorption. Consequently, the above conventional system cannot restrain the exhaust sensor output from deviating from normal under the influence of the adsorbable species.

DISCLOSURE OF INVENTION

The present invention has been made to solve the above problems and provides an exhaust sensor controller that is capable of properly detecting the status of an exhaust gas immediately after internal combustion engine startup while minimizing the influence of exhaust sensor output deviation, which is caused by an adsorbable species.

The above object is achieved by an exhaust sensor controller according to a first aspect of the present invention. The controller controls an exhaust sensor mounted in an exhaust path of an internal combustion engine. The exhaust sensor includes a sensor element for generating an output in accordance with the status of an exhaust gas and a heater for heating the sensor element. The exhaust sensor controller includes a heater control unit for continuing power supply control over the heater until the ambient temperature for the exhaust sensor drops below 80° C. after the internal combustion engine is stopped.

In a first aspect of the present invention, power supply control is continued over a heater of an exhaust sensor until the ambient temperature for the exhaust sensor drops below 80° C. This makes it possible to prevent the temperature of an element of the sensor from lowering to reach the adsorption temperature region. As a result, the present invention effectively restrains the exhaust sensor output from deviating from normal under the influence of the adsorbable species by reducing the amount of adsorbable species that becomes adsorbed to the exhaust sensor after an internal combustion engine stop.

In a second aspect of the present invention, the exhaust sensor according to the first aspect of the present invention may further include an element temperature acquisition unit for acquiring the temperature of the sensor element. The heater control unit includes an after-stop power supply control unit for controlling the heater with a predetermined temperature between 300° C. and 500° C. set as a target temperature for the sensor element after the internal combustion engine is stopped.

In a second aspect of the present invention, control can be exercised after an internal combustion engine stop so that the temperature of the sensor element is maintained within a target temperature range from 300° C. to 500° C. When control is exercised in this manner, the sensor element temperature can be efficiently maintained above the adsorption temperature region without extra power consumption.

In a third aspect of the present invention, the exhaust sensor according to the first or second aspect of the present invention may further includes a heater control unit in which a stop moment exhaust temperature estimation unit and a temperature condition determination unit are provided. The stop moment exhaust temperature estimation unit estimates the exhaust path temperature at a stop moment of the internal combustion engine. The temperature condition determination unit determines whether the exhaust path temperature is below 80° C. based on the exhaust path temperature at the stop moment and the elapsed time after the internal combustion engine is stopped.

In a third aspect of the present invention, it is possible to estimate the exhaust path temperature at a moment of an internal combustion engine stop, determine the elapsed time after the internal combustion engine stop, and check, in accordance with the estimated exhaust path temperature and determined elapsed time, whether the exhaust path temperature is below 80° C. As a result, the present invention can continue heating the sensor element for an appropriate period of time without directly detecting the exhaust path temperature.

The above object is also achieved by an exhaust sensor controller according to a fourth aspect of the present invention. The controller controls an exhaust sensor mounted in an exhaust path of an internal combustion engine. The exhaust sensor includes a sensor element for generating an output in accordance with the status of an exhaust gas and a heater for heating the sensor element. The exhaust sensor controller includes a recovery value counting unit for counting the elapsed time or the cumulative intake air amount after internal combustion engine startup as a characteristics recovery value. A heater control unit is provided for controlling the heater with a recovery target temperature, which is higher than a normal target temperature, set as a target temperature for the sensor element until the characteristics recovery value reaches a recovery determination value. A cumulative lean time counting unit is also provided for counting, after internal combustion engine startup, the cumulative length of time during which the air-fuel ratio is lean. Further, a determination value correction unit is provided for increasing the characteristics recovery value or decreasing the recovery determination value with an increase in the cumulative length of time.

In a fourth aspect of the present invention, the early desorption of the adsorbable species can be promoted by controlling the sensor element to maintain it at a high temperature until the elapsed time or the cumulative intake air amount after internal combustion engine startup (characteristics recovery value) reaches a recovery determination value. As a result, the present invention can eliminate the exhaust sensor output deviation, which is caused by the adsorbable species, immediately after internal combustion engine startup. Further, the present invention ensures that the longer the period of time subsequent to internal combustion engine startup during which the air-fuel ratio is lean, the earlier the characteristics recovery value reaches the recovery determination value. In other words, it is possible to reduce the length of time during which control is exercised to maintain the sensor element at a high temperature. When the air-fuel ratio is lean, adsorbable species desorption is promoted. Therefore, the longer the period of time during which the air-fuel ratio is lean, the shorter the time required for adsorbable species desorption. The present invention makes it possible to minimize the time during which the sensor element is maintained at a high temperature in accordance with the time required for adsorbable species desorption.

The above object is also achieved by an exhaust sensor controller according to a fifth aspect of the present invention. The controller controls an exhaust sensor mounted in an exhaust path of an internal combustion engine. The exhaust sensor includes a sensor element for generating an output in accordance with the status of an exhaust gas and a heater for heating the sensor element. The exhaust sensor controller includes a recovery value counting unit for counting the elapsed time or the cumulative intake air amount after internal combustion engine startup as a characteristics recovery value. A heater control unit is provided for controlling the heater with a recovery target temperature, which is higher than a normal target temperature, set as a target temperature for the sensor element until the characteristics recovery value reaches a recovery determination value. A stop period counting unit is also provided for counting the stop period during which the internal combustion engine is stopped. Further, a determination value correction unit is provided for decreasing the characteristics recovery value or increasing the recovery determination value with an increase in the stop period during which the internal combustion engine is stopped.

In a fifth aspect of the present invention, the early desorption of the adsorbable species can be promoted by exercising control to maintain the sensor element at a high temperature until the recovery determination value is reached by the elapsed time or the cumulative intake air amount after internal combustion engine startup (characteristics recovery value). As a result, the present invention can eliminate the exhaust sensor output deviation, which is caused by the adsorbable species, immediately after internal combustion engine startup. Further, the present invention ensures that the longer the period of time during which the internal combustion engine is stopped, the later the characteristics recovery value reaches the recovery determination value. In other words, it is possible to exercise control to maintain the sensor element at a high temperature for an extended period of time. The longer the period of time during which the internal combustion engine is stopped, the larger the amount of adsorbable species adsorption. Therefore, the longer the period of time during which the internal combustion engine is stopped, the longer the time required for adsorbable species desorption. The present invention makes it possible to minimize the time during which the sensor element is maintained at a high temperature in accordance with the time required for adsorbable species desorption.

The above object is also achieved by an exhaust sensor controller according to a sixth aspect of the present invention. The controller controls an exhaust sensor mounted in an exhaust path of an internal combustion engine. The exhaust sensor includes a sensor element for generating an output in accordance with the status of an exhaust gas and a heater for heating the sensor element. The exhaust sensor controller includes a cumulative lean time counting unit for counting, after internal combustion engine startup, the cumulative length of time during which the air-fuel ratio is lean. The exhaust sensor controller also includes a heater control unit for controlling the heater with a recovery target temperature, which is higher than a normal target temperature, set as a target temperature for the sensor element until the cumulative length of time reaches a recovery determination value.

In a sixth aspect of the present invention, the early desorption of the adsorbable species can be promoted by exercising control to maintain the sensor element at a high temperature until the cumulative time during which the air-fuel ratio is lean reaches the recovery determination value after internal combustion engine startup. Since adsorbable species desorption is promoted when the air-fuel ratio is lean, it can be concluded that adsorbable species desorption is completed when the cumulative lean time reaches the recovery determination value. As a result, when it is concluded that adsorbable species desorption is completed after internal combustion engine startup, the present invention can properly terminate a high-temperature control process for the exhaust sensor.

In a seventh aspect of the present invention, the exhaust sensor controller according to the sixth aspect of the present invention may further includes a recovery value counting unit for counting the elapsed time or the cumulative intake air amount after internal combustion engine startup as a characteristics recovery value. The controller also includes a determination value correction unit for increasing the cumulative length of time or decreasing the recovery determination value with an increase in the characteristics recovery value.

A seventh aspect of the present invention ensures that the time required for the cumulative lean time to reach the recovery determination value decreases with an increase in the elapsed time or the cumulative intake air amount after internal combustion engine startup (characteristics recovery value). In other words, it is possible to reduce the period of time during which control is exercised to maintain the sensor element at a high temperature. Adsorbable species desorption progresses with an increase in the characteristics recovery value no matter whether the air-fuel ratio is lean. The present invention makes it possible to take the progress of adsorbable species desorption into consideration and accurately minimize the period of time during which high-temperature control is exercised over the exhaust sensor.

In an eighth aspect of the present invention, the exhaust sensor according to the sixth or seventh aspect of the present invention may further includes a stop period counting unit for counting the stop period during which the internal combustion engine is stopped. The controller also includes a determination value correction unit for decreasing the cumulative length of time or increasing the recovery determination value with an increase in the stop period during which the internal combustion engine is stopped.

In an eighth aspect of the present invention, the time at which the cumulative lean time reaches to the recovery determination value delays with an increase in the stop period during which the internal combustion engine is stopped. In other words, the period during which the sensor element is maintained at a high temperature is enlarged with the increase of the stop period. Since the amount of adsorbable species adsorption increases with an increase in the stop period during which the internal combustion engine is stopped, the longer the time during which the internal combustion engine is stopped, the longer the time required for adsorbable species desorption. The present invention makes it possible to take the resulting influence into consideration and accurately minimize the period of time during which high-temperature control is exercised over the exhaust sensor.

The above object is also achieved by an exhaust sensor controller according to a ninth aspect of the present invention. The controller controls an exhaust sensor mounted in an exhaust path of an internal combustion engine. The exhaust sensor includes a sensor element for generating an output in accordance with the status of an exhaust gas and a heater for heating the sensor element. The exhaust sensor controller includes an element temperature acquisition unit for acquiring the temperature of the sensor element. The controller also includes a desorption progress value counting unit for counting the elapsed time or the cumulative intake air amount after the temperature of the sensor element reaches the desorption temperature of an adsorbable species adsorbed by the sensor element as a desorption progress value. An output correction unit is provided for correcting the output of the exhaust sensor in accordance with a sensor output correction value. Further, a correction value calculation unit is provided for decreasing the sensor output correction value with an increase in the desorption progress value.

In a ninth aspect of the present invention, it is possible to count the elapsed time or the cumulative intake air amount after the temperature of the sensor element reaches the adsorbable species desorption temperature as a desorption progress value. A deviation is superposed over the exhaust sensor output when the adsorbable species becomes desorbed. The amount of such a deviation decreases with an increase in the desorption progress value. In the present invention, the exhaust sensor output is corrected by a sensor output correction value. The sensor output correction value decreases with an increase in the desorption progress value. As a result, the present invention makes it possible to accurately compensate for an output deviation, which is caused by adsorbable species desorption, and obtain a sensor output that is not affected by the adsorbable species.

In a tenth aspect of the present invention, the exhaust sensor according to the ninth aspect of the present invention may further includes a stop period counting unit for counting the stop period during which the internal combustion engine is stopped. The correction value calculation unit includes initial value setup unit, which increases the initial value for the sensor output correction value with an increase in the stop period.

A tenth aspect of the present invention ensures that the initial value for the sensor output correction value increases with an increase in the period during which the internal combustion engine is stopped. If the internal combustion engine is stopped for a long period of time, an increased amount of adsorbable species becomes adsorbed; therefore, the sensor output is likely to suffer significant deviation. The present invention can accurately correct the sensor output because the amount of adsorbable species adsorption can be reflected in the initial value for the sensor output correction value.

BRIEF DESCRIPTION OF DRAWINGS

FIG. 6 shows an example of a map that is referenced by the routine shown in FIG. 5;

BEST MODE FOR CARRYING OUT THE INVENTION

First Embodiment

[Hardware Configuration of the First Embodiment]

Figure 1:
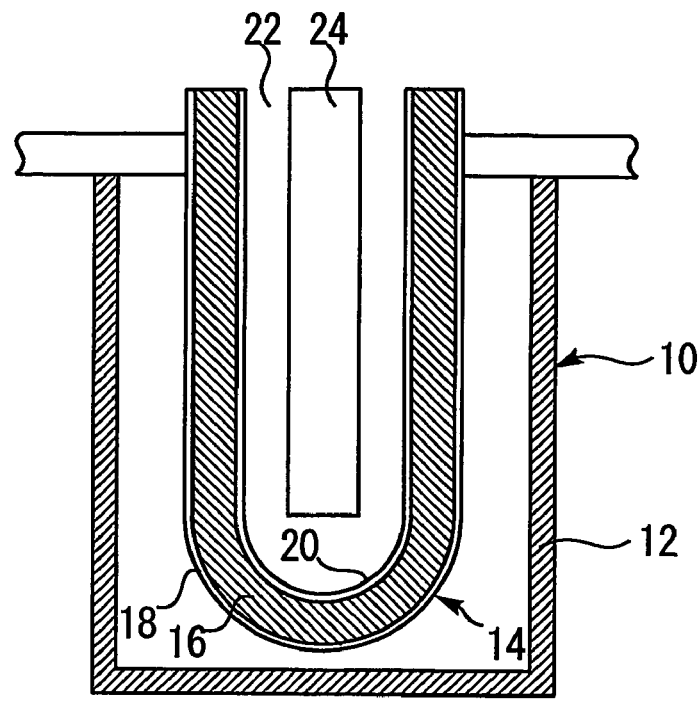
FIG. 1 illustrates the structure of an oxygen sensor according to a first embodiment of the present invention.

FIG. 1 illustrates the configuration of an oxygen sensor 10 that is used according to a first embodiment of the present invention. The oxygen sensor 10 shown in FIG. 1 is positioned in an exhaust path of an internal combustion engine to detect whether oxygen exists in an exhaust gas, that is, determine whether the exhaust air-fuel ratio is lean or rich.

The oxygen sensor 10 is provided with a cover 12. The cover 12 is installed over the exhaust path in such a manner that it is exposed to the exhaust gas. The cover 12 is internally provided with a hole (not shown) for exhaust gas guidance. A sensor element 14 is mounted within the cover 12. The sensor element 14 is shaped like a tube, one end of which (lower end in FIG. 1) is closed. The sensor element 14 comprises a solid electrolyte layer 16, an exhaust electrode 18, and an atmospheric air electrode 20. The solid electrolyte layer 16 comprises a $ZrO_2$ solid electrolyte. The exhaust electrode 18 and atmospheric air electrode 20, which both consist of a highly catalytic Pt based metal, are formed respectively on the outer side and inner side of the solid electrolyte layer 16.

An atmospheric air chamber 22, which is exposed to atmosphere, is formed inside the sensor element 14. A heater 24 for heating the sensor element 14 is positioned in the atmospheric air chamber 22. When heated to an activity temperature between approximately 550° C. and 600° C., the sensor element 14 becomes active and ready to generate a steady output. When a control circuit, which will be described later, exercises power supply control, the heater 24 can heat the sensor element 14 to the above-mentioned activity temperature.

Figure 2:
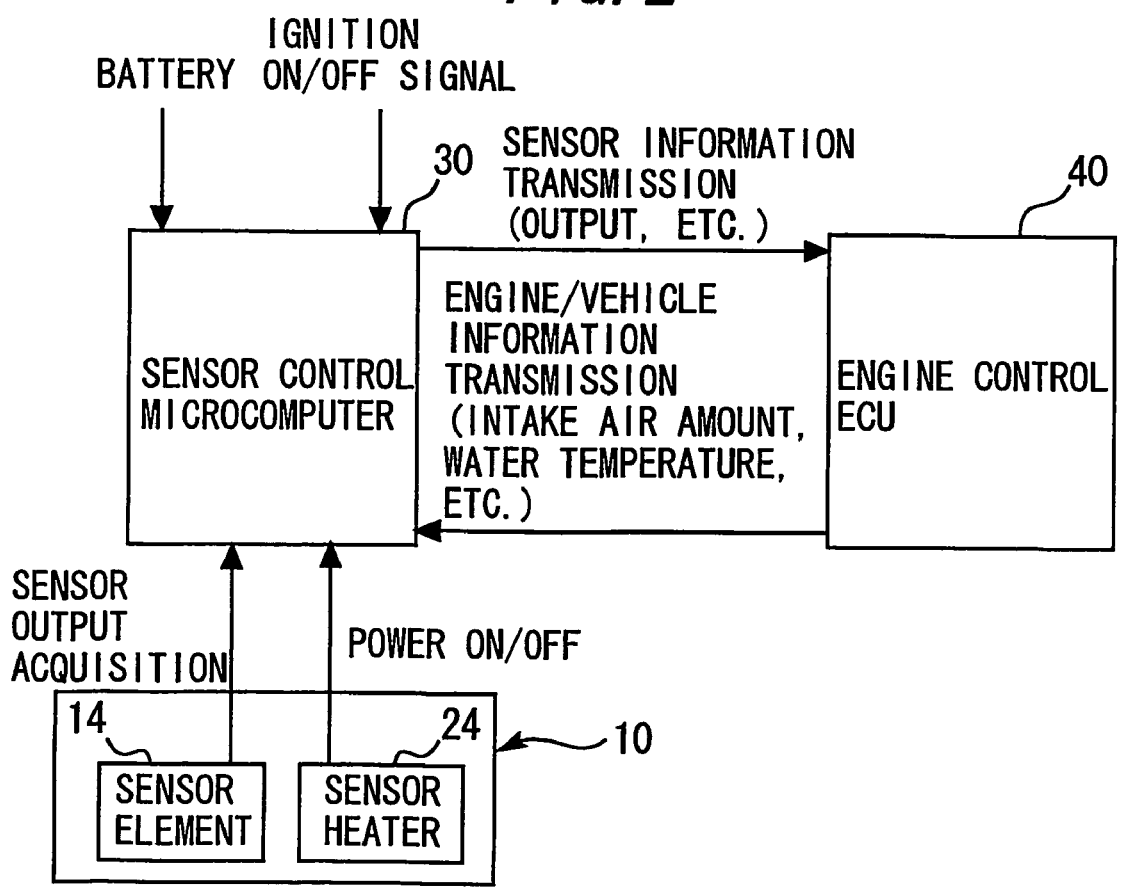
FIG. 2 is a block diagram illustrating the configuration of a controller according to the first embodiment of the present invention.

FIG. 2 is a block diagram illustrating a controller for the oxygen sensor 10. A control circuit according to the present embodiment comprises a sensor control microcomputer 30 (hereinafter abbreviated to microcomputer 30) and an engine control ECU (Electronic Control Unit) 40 (hereinafter abbreviated to ECU 40). A battery supplies electrical power to the microcomputer 30. Further, a vehicle's ignition switch (IG switch) supplies an ignition ON/OFF signal to the microcomputer 30. The microcomputer 30 incorporates a timer circuit, which allows the microcomputer 30 to operate for a predetermined period of time after ignition switch OFF.

The microcomputer 30 is connected to the sensor element 14 of the oxygen sensor 10 (strictly, the exhaust electrode 18 and atmospheric air electrode 20) and the heater 24. The exhaust electrode 18 and the atmospheric air electrode 20 of the sensor element 14 generate electromotive force therebetween. The electromotive force generated in this manner varies depending on whether oxygen exists in the exhaust gas. The microcomputer 30 acquires the electromotive force as a sensor output and determines whether oxygen exists in the exhaust gas, that is, whether the exhaust air-fuel ratio is lean or rich.

Further, the microcomputer 30 has a function for detecting the impedance of the sensor element 14 by a publicly known method. Since the impedance of the sensor element 14 corresponds to the temperature of the sensor element 14, the microcomputer 30 can estimate the sensor element temperature from the impedance. The microcomputer 30 can therefore exercise feedback control over power supply to the heater 24 so that the sensor element temperature reaches a target level.

The microcomputer and ECU 40 exchange sensor information (the output from the oxygen sensor 10 or the like) and engine/vehicle information (intake air amount, water temperature, etc.). The ECU 40 uses the received sensor information, for instance, to provide air-fuel ratio feedback for the fuel injection amount. The microcomputer 30 uses the received vehicle information, for instance, to estimate the exhaust path temperature.

[Influence of Adsorbable Species]

Figure 3A:
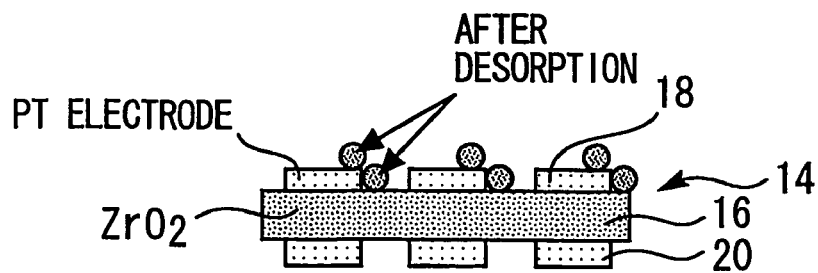
FIG. 3A shows how an adsorbable species is adsorbed by a sensor element after an internal combustion engine stop.
Figure 3B:
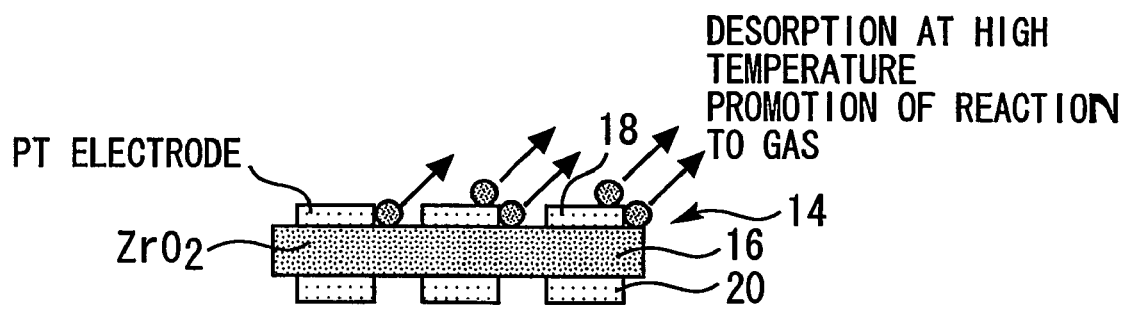
FIG. 3B shows how the adsorbable species affects the oxygen sensor output after internal combustion engine startup.

FIG. 3A illustrates how the adsorbable species becomes adsorbed to the sensor element 14 after an internal combustion engine stop. FIG. 3B illustrates how the adsorbable species affects the output of the oxygen sensor 10 after internal combustion engine startup.

As described earlier, the oxygen sensor 10 is used while the exhaust electrode 18 is exposed to the exhaust gas. The exhaust gas contains $H_2O$, $CO_2$, $O_2$, and various other constituents. While the oxygen sensor 10 is active, such constituents do not become adsorbed to the exhaust electrode 18. However, a chemical adsorptive reaction may occur between such constituents and the exhaust electrode 18 when the temperature of the sensor element 14 lowers after an internal combustion engine stop.

The applicant of the present invention has found that the above adsorptive reaction is likely to occur particularly when the temperature of the sensor element 14 is below 300° C. In other words, the applicant of the present invention has found that the upper limit on the temperature region in which the adsorbable species becomes adsorbed to the sensor element 14 (adsorption temperature region) is approximately 300° C. Since the power supply to the heater 24 stops after the internal combustion engine 10 is stopped, the temperature of the sensor element 14 inevitably lowers to an adsorption temperature region, which is below 300° C. As a result, the adsorbable species inevitably becomes adsorbed to the surface of the sensor element 14 after the internal combustion engine 10 is stopped, as shown in FIG. 3A.

When the internal combustion engine starts up, the power supply to the heater 24 starts. Therefore, the temperature of the sensor element 14 rises. When the temperature of the sensor element 14 rises above the adsorption temperature region, that is, exceeds 300° C., the adsorbable species begins to become desorbed from the surface of the exhaust electrode 18 as shown in FIG. 3B and various reactions vigorously occur on the surface. In such an instance, because $H_2$, which is a reducing substance, is generated on the surface of the exhaust electrode 18 and because the number of points for reaction with oxygen on the exhaust electrode 18 decreases due to the presence of the adsorbable species, the output of the oxygen sensor 10 is temporarily shifted toward the rich side. When the temperature of the sensor element 14 rises and the desorption of the adsorbable species progresses, the rich displacement of the sensor output is compensated for in the end.

[Solutions Provided by the First Embodiment]

To accurately control the air-fuel ratio of the internal combustion engine immediately after it is started up, it is preferred that the output of the oxygen sensor 10 be available as soon as possible. The sensor output cannot be directly used if it is affected by rich displacement. It is therefore preferred that adsorbable species desorption be completed early. To assure early completion of adsorbable species desorption, it is preferred that the amount of adsorbable species adsorbed by the sensor element 14 during an internal combustion engine stop be minimized.

Figure 4:
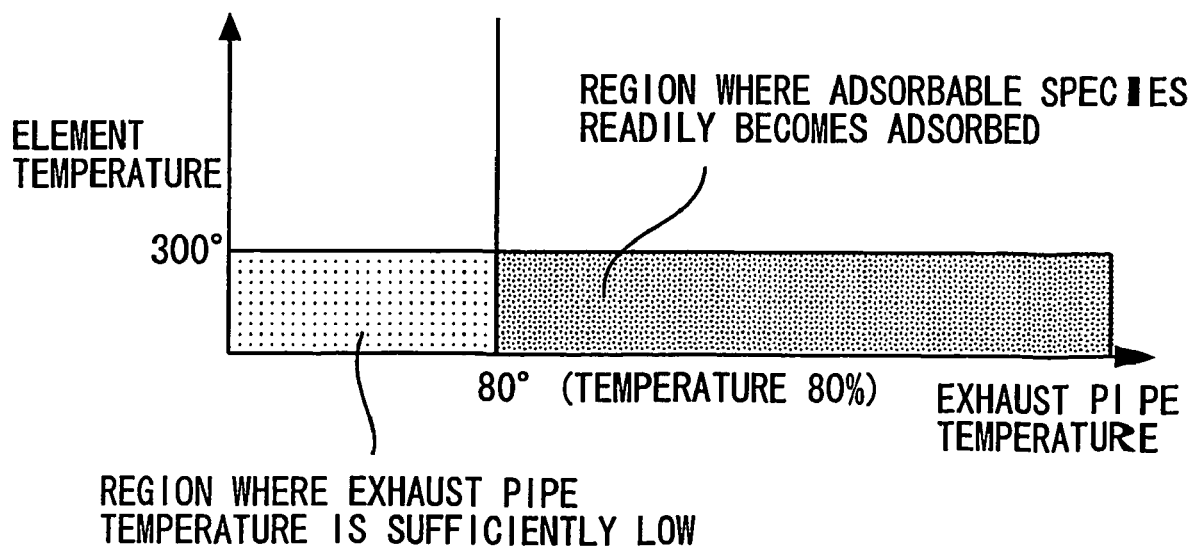
FIG. 4 schematically shows the relationship among the temperature of an exhaust pipe, the temperature of a sensor element and the readiness with which the adsorbable species adsorbs to the sensor element.

FIG. 4 schematically shows the relationship among the temperature of an exhaust pipe, the temperature of a sensor element and the readiness with which the adsorbable species adsorbs to the sensor element. As indicated in FIG. 4, the applicant of the present invention has found that the readiness with which the adsorbable species becomes adsorbed significantly varies with the temperature of the sensor element 14 and the temperature of an exhaust pipe. That is, the applicant of the present invention has found that if the temperature of the sensor element 14 is above 300° C., adsorbable species adsorption does not occur without regard to the exhaust pipe temperature. If the element temperature is below 300° C. and within the adsorption temperature region, adsorbable species adsorption readily occurs while the exhaust pipe temperature is above 80° C., but does not readily occur while the exhaust pipe temperature is below 80° C.

According to the characteristics shown in FIG. 4, adsorbable species adsorption does not occur if the sensor element 14 is maintained at a temperature higher than 300° C. during the time interval between the instant at which the internal combustion engine is stopped and the instant at which the exhaust pipe temperature drops below 80° C. (condition 1). If the element temperature drops below 300° C. after the exhaust pipe temperature is below 80° C. (condition 2), it is possible to sufficiently restrain the amount of adsorbable species that is generated while the element temperature lowers to a normal level. Under these circumstances, the present embodiment controls the heater 24 for the oxygen sensor 10 so that conditions 1 and 2 above are met after the internal combustion engine's ignition switch is turned OFF.

[Process Performed by the First Embodiment]

Figure 5:
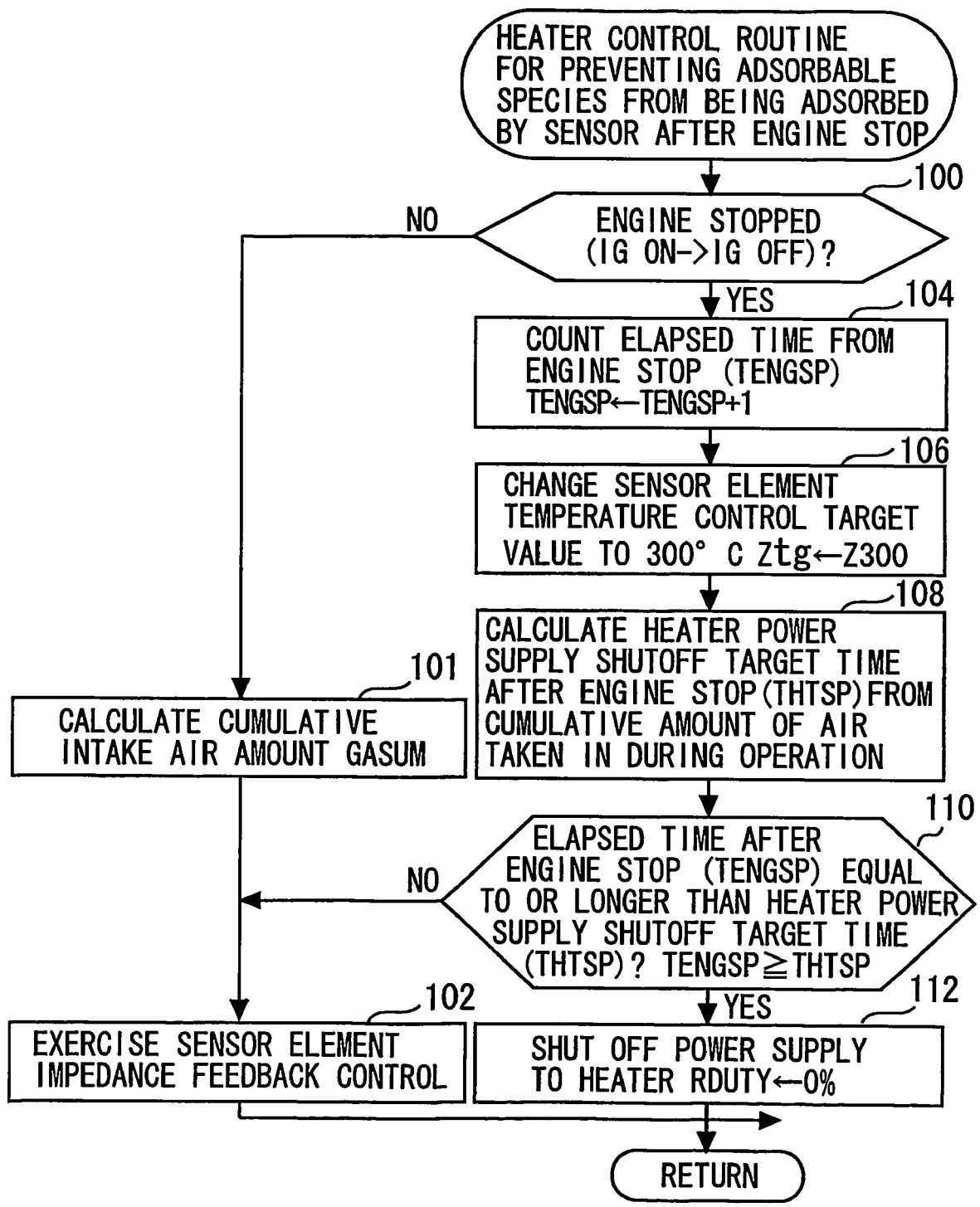
FIG. 5 is a flowchart illustrating a routine that is executed by the first embodiment of the present invention.

FIG. 5 is a flowchart illustrating a routine that the microcomputer 30 executes to implement the above functionality. The routine shown in FIG. 5 is started upon internal combustion engine startup and then repeatedly executed at predetermined time intervals.

In the routine shown in FIG. 5, step 100 is first performed to determine whether it is recognized that the internal combustion engine is stopped. More specifically, the routine checks whether an OFF output is generated by the ignition switch. If the stop of the internal combustion engine is not recognized in step 100, step 101 is performed to calculate the cumulative value GAsum of the intake air amount Ga. Next, step 102 is performed to exercise impedance feedback control over the oxygen sensor 10. A normal value (which represents an appropriate temperature within the range from 550° C. to 600° C.) is employed as a target temperature for the sensor element 14. Therefore, when processing step 102 is performed, control is exercised to maintain the element at an activity temperature between 550° C. and 600° C.

If, on the other hand, the stop of the internal combustion engine is recognized in step 100, step 104 is performed to increment a counter TENGSP that counts the elapsed time after an internal combustion engine stop. It is assumed that the value of counter TENGSP is reset to zero when an initialization process is performed upon internal combustion engine startup. For the sake of simplicity, the count reached by counter TENGSP will be referred to as the "elapsed time TENGSP".

Next, the target temperature for the sensor element 14 changes to 300° C., that is, the lower-limit temperature that is outside the adsorption temperature region. More specifically, a target impedance Ztg that is used for impedance feedback control is changed to a value Z300 that corresponds to an element temperature of 300° C. (step 106).

The target time interval between the instant at which the internal combustion engine is stopped and the instant at which the power supply to the heater 24 is stopped (hereinafter referred to as the "target stop time THTSP") is then calculated in accordance with the intake air amount cumulative value GAsum (step 108).

In the present embodiment, the target stop time THTSP should coincide with the time required for the exhaust pipe temperature to drop below 80° C. This required time increases with an increase in the exhaust pipe temperature that prevails while the internal combustion engine is stopped. Meanwhile, the exhaust pipe temperature gradually rises to a convergence value after internal combustion engine startup. It is therefore believed that the temperature increases with an increase in the intake air amount cumulative value GAsum. Thus, it is conceivable that the above-mentioned required time, which should coincide with the target stop time THTSP, increases (up to an upper limit) with an increase in the intake air amount cumulative value GAsum, which is calculated at the time of an internal combustion engine stop.

FIG. 6 shows an example of a map that the microcomputer 30 references to calculate the target stop time THTSP in step 108 above. The map is set so that the target stop time THTSP increases with an increase in the intake air amount cumulative value GAsum and coincides with the above-mentioned required time. According to the process performed in step 108, the time that accurately matches the required time interval between the instant at which the internal combustion engine is stopped and the instant at which the exhaust pipe temperature drops below 80° C. can be set as the target stop time THTSP.

Next, step 110 is performed to determine whether the elapsed time TENGSP after an internal combustion engine stop has reached the target stop time THTSP. If the determination result does not indicate that TENGSP≧THTSP, it can be estimated that the exhaust pipe temperature is not yet below 80° C. In this instance, impedance feedback control is subsequently exercised in step 102. Since the target temperature for the element is set to 300° C. by the process performed in step 104, the heater 24 is controlled so that the sensor element 14 reaches a temperature of 300° C.

For the purpose of controlling the heater 24 to attain a sensor element temperature of 300° C., the above process is repeatedly performed until it is found that TENGSP≧THTSP, that is, until it is estimated that the exhaust pipe temperature is below 80° C. If the temperature of the sensor element 14 does not drop below 300° C., the adsorbable species does not become adsorbed to the sensor element 14. If control is exercised to maintain the sensor element 14 at a temperature of 300° C., it is possible to avoid adsorbable species adsorption while the power consumption is minimized. As a result, the controller according to the present embodiment can efficiently restrain adsorbable species adsorption during the time interval between the instant at which the internal combustion engine is stopped and the instant at which the exhaust pipe temperature drops below 80° C.

When an adequate amount of time elapses after an internal combustion engine stop, the determination result obtained in step 110 indicates that TENGSP≧THTSP. In this instance, it can be estimated that the exhaust pipe temperature is below 80° C. When it is found that TENGSP≧THTSP, the routine shown in FIG. 5 shuts off the power supply to the heater 24 (sets the heater power supply duty RDUTY to zero) and causes the microcomputer 30 to terminate its heater control (step 112).

After the power supply to the heater 24 is shut off, the temperature of the sensor element 14 decreases from 300° C. to a normal temperature. During such an element temperature drop, the adsorbable species becomes adsorbed to the sensor element 14. However, the ambient temperature and humidity for the sensor element 14 are no longer high. Therefore, a small amount of adsorbable species becomes adsorbed. If the amount of adsorbable species adsorption is small, the influence of the adsorbable species immediately disappears after a subsequent internal combustion engine restart. As a result, the controller according to the present embodiment minimizes the influence of oxygen sensor output deviation, which is caused by the adsorbable species, and begins to properly detect the exhaust gas status immediately after internal combustion engine startup.

[Example of a Modified Process Performed by the First Embodiment]

A modified process performed by the first embodiment will now be described. The adsorbable species, which causes the oxygen sensor output to suffer rich displacement, becomes chemically adsorbed to the oxygen sensor 10. In addition, the carbon content of the exhaust gas may also become adsorbed to the oxygen sensor 10. The carbon content can be burned off by heating the sensor element 14 to a temperature, for instance, of approximately 700° C.

As described earlier, the controller according to the present embodiment continues to control the heater 24 until the exhaust pipe path temperature drops below 80° C. after an internal combustion engine stop. If the sensor element 14 is temporarily heated to a temperature of 700° C. in such an instance, the carbon content can be burned off while reducing the amount of adsorbable species adsorption.

Figure 7:
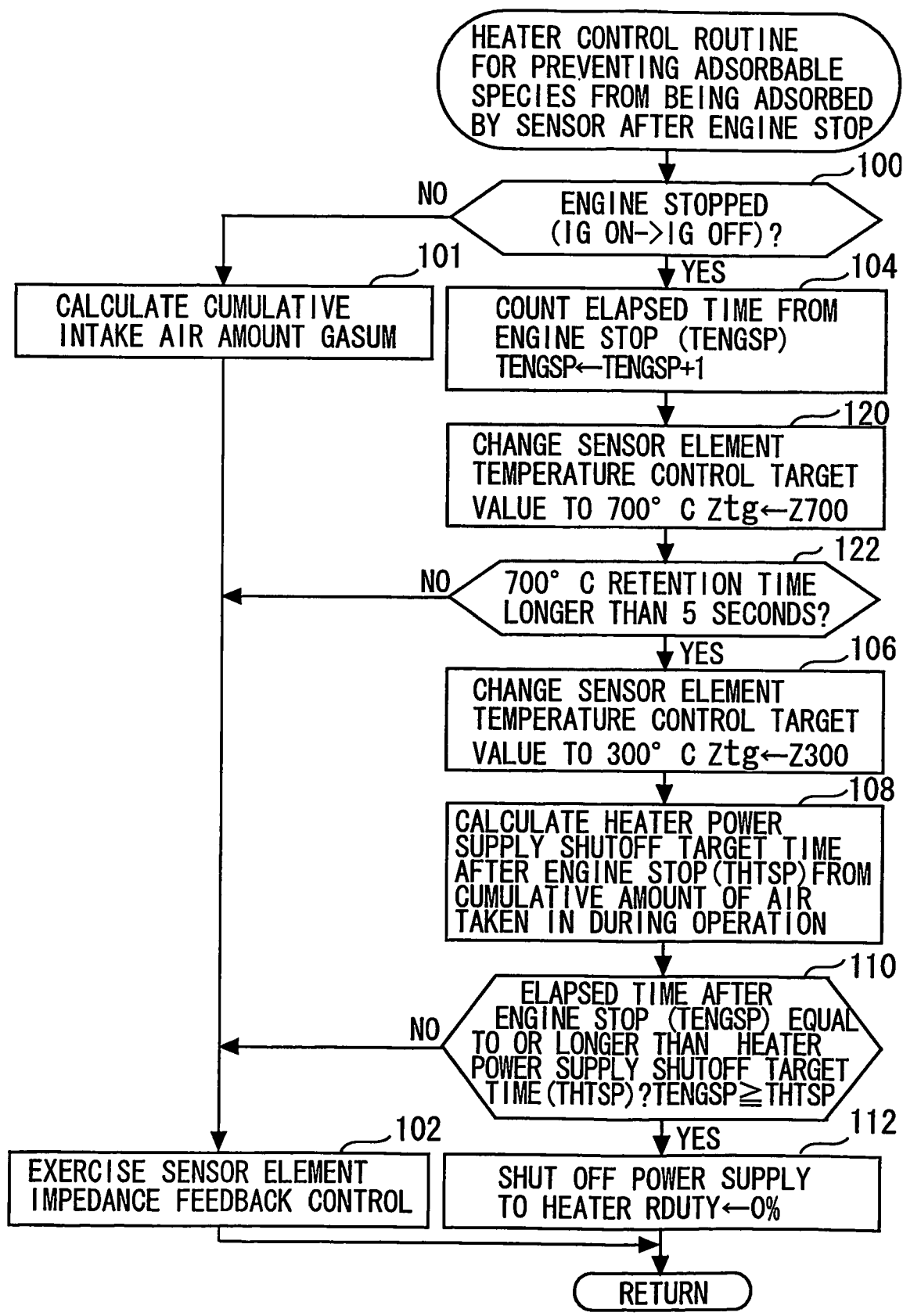
FIG. 7 is a flowchart illustrating a modified routine that is executed by the first embodiment of the present invention.

FIG. 7 shows a routine that is executed to implement the above functionality. The routine shown in FIG. 7 is the same as the routine shown in FIG. 5 except that a carbon burn-off process is inserted between steps 104 and 106. As regards the steps in FIG. 7 that are the same as the steps in FIG. 5, their description is omitted or abridged with the same reference numerals assigned.

If the determination result obtained in step 100 indicates that the internal combustion engine is stopped, the routine shown in FIG. 7 performs processing step 104 and then changes the target temperature for the sensor element 14 to 700° C., that is, to a temperature for burning off the carbon content. More specifically, the target impedance Ztg for use in impedance feedback control is changed to a value Z700 that corresponds to an element temperature of 700° C. (step 120).

Next, step 122 is performed to determine whether the length of time during which the sensor element 14 is maintained at 700° C. has exceeded 5 seconds. Step 102 is performed to exercise impedance feedback control with the target temperature set at 700° C. until it is determined that the sensor element 14 has been maintained at 700° C. for a period of longer than 5 seconds. After it is determined that the sensor element 14 has been maintained at 700° C. for a period of longer than 5 seconds, step 106 is performed to change the target temperature for the sensor element 14 to 300° C.

According to the above processing steps, the sensor element 14 is maintained at 700° C. for a period of approximately 5 seconds after an internal combustion engine stop. Subsequently, control is exercised to maintain the sensor element temperature at 300° C. until the exhaust pipe temperature drops below 80° C. If the sensor-element 14 is maintained at 700° C. for a period of 5 seconds, the carbon attached to the sensor element 14 burns off. As a result, when the microcomputer 30 executes the routine shown in FIG. 7, the carbon content can be burned off immediately after an internal combustion engine stop while restraining the amount of adsorbable species adsorption to the sensor element 14 during a temperature drop process.

In the first embodiment, which is described above, the sensor mounted in the exhaust path is limited to the oxygen sensor 10. Alternatively, however, an air-fuel ratio sensor that generates an output linear with respect to the exhaust air-fuel ratio may be used in place of the oxygen sensor. This also holds true for the other embodiments described later.

In the first embodiment, which is described above, the target temperature for the sensor element 14 is set to 300° C. for the purpose of avoiding adsorbable species adsorption with a minimum of power consumption during the time interval between the instant at which the internal combustion engine is stopped and the instant at which the exhaust pipe temperature reaches 80° C. However, an alternative target temperature may be set for the sensor element 14. More specifically, a target element temperature of 300° C. or higher is acceptable. From the viewpoint of power consumption reduction, it is preferred that the target element temperature be between 300° C. and 500° C. or so.

In the first embodiment, which is described above, "heater control unit" according to the first aspect of the present invention is implemented when the microcomputer 30 performs processing steps 102 through 110. Further, "element temperature acquisition unit" according to the second aspect of the present invention is implemented when the microcomputer 30 acquires the sensor element impedance, and "after-stop power supply control unit" according to the second aspect of the present invention is implemented when the microcomputer 30 performs processing steps 106 and 102 in order named. Furthermore, "stop period exhaust temperature estimation unit" and "temperature condition determination unit" according to the third aspect of the present invention are implemented when the microcomputer 30 performs processing steps 101, 108, and 110.

Second Embodiment

[Features of the Second Embodiment]

The second embodiment of the present invention will now be described with reference to FIG. 8. The controller according to the second embodiment is implemented when the hardware configuration shown in FIG. 1 or 2 is employed to let the microcomputer 30 execute a routine shown in FIG. 8 in place of or together with the routine shown in FIG. 5 or 7.

The controller according to the first embodiment can reduce the amount of adsorbable species that becomes adsorbed to the sensor element 14 during an internal combustion engine stop. However, the complete prevention of the adsorbable species adsorption is impossible by the controller. The controller according to the first embodiment cannot prevent the output of the oxygen sensor 10 from temporarily suffering rich displacement after internal combustion engine startup.

The adsorbable species adsorbed by the sensor element 14 begins to become desorbed when the temperature of the sensor element 14 exceeds 300° C. The higher the temperature of the sensor element 14, the higher the speed of desorption. Therefore, when the sensor element 14 is set to a temperature (e.g., 800° C.) higher than a normal target temperature (550° C. to 600° C. or so), the time required for adsorbable species desorption can be reduced to shorten the length of time during which the sensor output suffers rich displacement. This control process is hereinafter referred to as "high-temperature control".

From the viewpoint of sensor element durability and power consumption, it is preferred that the length of time during which control is exercised to maintain the sensor element 14 at a temperature higher than the normal target temperature be minimized. Therefore, if such high-temperature control is exercised over the sensor element 14, it is preferred that such high-temperature control terminate immediately after completion of adsorbable species desorption.

The applicant of the present invention has found that the speed of adsorbable species desorption depends on not only the temperature of the sensor element 14 but also the air-fuel ratio of the exhaust gas surrounding the sensor element 14. More specifically, the applicant of the present invention has found that if the exhaust gas is an oxidative atmosphere, that is, if the exhaust air-fuel ratio is lean, adsorbable species desorption is accelerated because the adsorbable species generates $H_2$, which is a reducing substance, at the time of desorption. Therefore, the time required for the completion of adsorbable species desorption decreases with an increase in the "lean time", which represents the period of time subsequent to internal combustion engine startup during which the exhaust air-fuel ratio remains lean.

When the above requirements are considered, if the time required for adsorbable species desorption shows increase or decrease, the high-temperature control period for the sensor element 14 should be varied in accordance with the increase or decrease. Under these circumstances, the present invention exercises high-temperature control over the sensor element 14 while counting the cumulative lean time after internal combustion engine startup to ensure that the length of time during which high-temperature control is exercised decreases with an increase in the cumulative lean time.

[Process Performed by the Second Embodiment]

Figure 8:
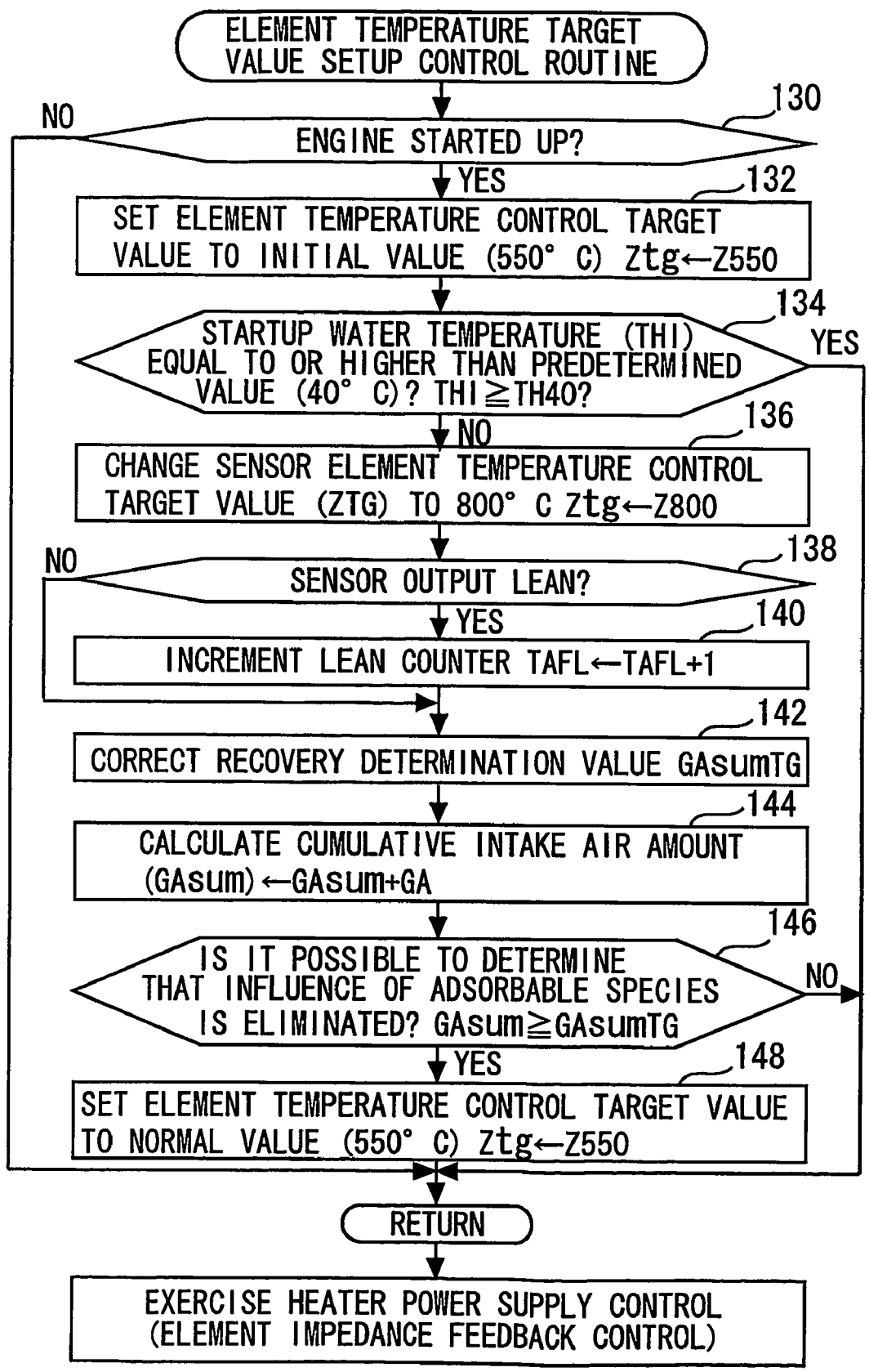
FIG. 8 is a flowchart illustrating a routine that is executed by a second embodiment of the present invention.

FIG. 8 is a flowchart illustrating a routine that the microcomputer 30 executes to implement the above functionality. The routine shown in FIG. 8 first performs step 130 to determine whether the internal combustion engine is started up. If the determination result obtained in step 130 does not indicate that the internal combustion engine is started up, the currently executed routine immediately terminates.

If, on the other hand, the determination result obtained in step 130 indicates that the internal combustion engine is started up, the target temperature for the sensor element 14 is set to an initial value (e.g., 550° C.). More specifically, the target impedance Ztg for use in impedance feedback control is set to a value Z550 that corresponds to a normal target temperature (550° C.) (step 132).

Next, step 134 is performed to determine whether the water temperature THI prevailing at internal combustion engine startup is equal to or higher than a predetermined determination temperature TH40 (e.g., 40° C.). If the determination result obtained in step 134 indicates that THI≧TH40, it can be concluded that the time interval between the last internal combustion engine stop and the internal combustion engine restart is short, and that the amount of adsorbable species adsorption is not enough to incur rich displacement on the sensor element 14. In such an instance, the current routine terminates while the target impedance Ztg remains to be Z550. After internal combustion engine startup, impedance feedback control begins to be exercised over the sensor element 14. In this instance, therefore, power supply control is exercised over the heater 24 so that the temperature of the sensor element 14 coincides with the normal target value (550° C.) hereinafter.

If, on the other hand, the determination result obtained in step 134 does not indicate that THI≧TH40, it can be concluded that the degree of adsorbable species adsorption to the sensor element 14 is unignorable. In such an instance, a high-temperature target value (e.g., 800° C.) is set for the sensor element 14 so as to exercise high-temperature control. More specifically, the target impedance Ztg for use in impedance feedback control is set to a value Z800 that corresponds to the high-temperature target value (800° C.) (step 136).

Although the high-temperature target value is set to 800° C. as an example, an alternative high-temperature target value may also be used. The high-temperature target value should be higher than the normal target value so as to promote the desorption of the adsorbable species. For example, a high-temperature target value of approximately 700° C. will sufficiently promote desorption.

Next, step 138 is performed to determine whether the output of the oxygen sensor 10 is lean. The output characteristic of the oxygen sensor 10 that prevails while the sensor element 14 is heated to a temperature of approximately 800° C. does not significantly differ from the output characteristic of the oxygen sensor 10 that prevails while the sensor element 14 is maintained at a normal target temperature of approximately 550° C. Therefore, even when high-temperature control is in progress, the output of the oxygen sensor 10 indicates with certain accuracy whether the exhaust air-fuel ratio is lean.

As described earlier, the adsorbable species adsorbed by the sensor element 14 is urged to become desorbed in a lean atmosphere. Therefore, if it is found in step 138 above that the sensor output is lean, it can be concluded that adsorbable species desorption is vigorous. In such an instance, step 140 is first performed to increment a lean counter TAFL in order to reduce the duration of high-temperature control. Next, step 142 is performed to correct a recovery determination value GAsumTG in accordance with the count reached by the lean counter TAFL.

If, on the other hand, it is found in step 138 that the sensor output is not lean, it can be concluded that adsorbable species desorption is not particularly promoted. In this instance, the program flow skips processing steps 140 and 142 so that the recovery determination value GAsumTG prevailing during the preceding processing cycle is continuously used.

Next, the routine shown in FIG. 8 performs step 144 to calculate the cumulative value GAsum of the amount of air Ga that has been taken in since internal combustion engine startup. Step 146 is then performed to determine whether the recovery determination value GAsumTG is exceeded by the intake air amount Ga.

The microcomputer 30 stores an initial value for the recovery determination value GAsumTG. The initial value represents the cumulative value for the intake air amount GA that is required for the completion of adsorbable species desorption when high-temperature control is exercised over the sensor element 14 in a rich atmosphere. In step 142 above, the recovery determination value GAsumTG is corrected by reduced the length of time according to the counted value of the lean counter TAFL, that is, the length of time during which the exhaust path atmosphere is made lean and the adsorbable species desorption is promoted. As a result, the recovery determination value GAsumTG accurately corresponds to the cumulative air intake amount GAsum that is actually required for the completion of adsorbable species desorption.

Therefore, if the determination result obtained in step 146 does not indicate that GAsum≧GAsumTG, it can be concluded that adsorbable species desorption from the sensor element 14 is not completed. In such an instance, the current routine terminates while the target impedance Ztg is maintained at Z800, and high-temperature control is continuously exercised over the sensor element 14.

If, on the other hand, the determination result obtained in step 146 indicates that GAsum≧GAsumTG, it can be concluded that adsorbable species desorption from the sensor element 14 is completed. In this instance, the target temperature for impedance feedback control is changed to a normal value (550° C.). More specifically, the target impedance Ztg is changed to Z550 (step 148). When processing step 148 is performed, high-temperature control subsequently terminates and then normal impedance feedback control starts.

When the process described above is performed, high-temperature control is exercised after internal combustion engine startup so as to promote adsorbable species desorption and reduce the period of time during which the sensor output suffers rich displacement. Further, the process ensures that the completion of adsorbable species desorption precisely coincides with the end of high-temperature control. As a result, the controller according to the present embodiment minimizes the influence of oxygen sensor output deviation, which is caused by the adsorbable species, and begins to properly detect the exhaust gas status immediately after internal combustion engine startup without extra power consumption and without causing avoidable damage to the sensor element 14.

[Modifications of and Supplementary Information About the Second Embodiment]

The second embodiment, which is described above, checks whether the recovery determination value GAsumTG is reached by the cumulative intake air amount GAsum in order to determine whether adsorbable species desorption is completed. However, an alternative determination method may be used. For example, the above determination may be formulated by checking whether the duration of high-temperature control reaches to a target time (recovery determination value).

Further, the second embodiment, which is described above, ensures that the longer the lean time, the smaller the recovery determination value GAsumTG. In this manner, the second embodiment varies the duration of high-temperature control in accordance with the phenomenon in which adsorbable species desorption is promoted in a lean atmosphere. However, an alternative method may be used. More specifically, corrections may be made to increase the cumulative intake air amount GAsum with an increase in the lean time so that the duration of high-temperature control varies according to the phenomenon.

In the second embodiment, which is described above, "recovery value counting unit" according to the fourth aspect of the present invention is implemented when the microcomputer 30 performs processing step 144. Further, "heater control unit" according to the fourth aspect of the present invention is implemented when the microcomputer 30 performs processing steps 136 and 146. Furthermore, "cumulative lean time counting unit" according to the fourth aspect of the present invention is implemented when the microcomputer 30 performs processing steps 138 and 140. Moreover, "determination value correction unit" according to the fourth aspect of the present invention is implemented when the microcomputer 30 performs processing step 142.

Third Embodiment

[Features of the Third Embodiment]

The third embodiment of the present invention will now be described with reference to FIG. 9. The controller according to the third embodiment is implemented when the hardware configuration shown in FIG. 1 or 2 is employed to let the microcomputer 30 execute a routine shown in FIG. 9 in place of or together with the routine shown in FIG. 5 or 7.

The controller according to the second embodiment exercises high-temperature control over the sensor element 14 after internal combustion engine startup, thereby reducing the period of time during which the sensor output suffers rich displacement. The second embodiment considers the cumulative period of time after startup during which the air-fuel ratio is lean, and exercises high-temperature control until adsorbable species desorption is completed.

The time required for adsorbable species desorption increases with an increase in the amount of adsorbable species adsorption to the sensor element 14 at the startup of the internal combustion engine. The amount of the adsorbable species increases with an increase in the length of time during which the internal combustion engine is stopped. Therefore, the longer the internal combustion engine stop time, the longer the time required for adsorbable species desorption. The third embodiment varies the duration of high-temperature control in accordance with the internal combustion engine stop time in order to ensure that the duration of high-temperature control precisely coincides with the time required for adsorbable species desorption.

[Process Performed by the Third Embodiment]

Figure 9:
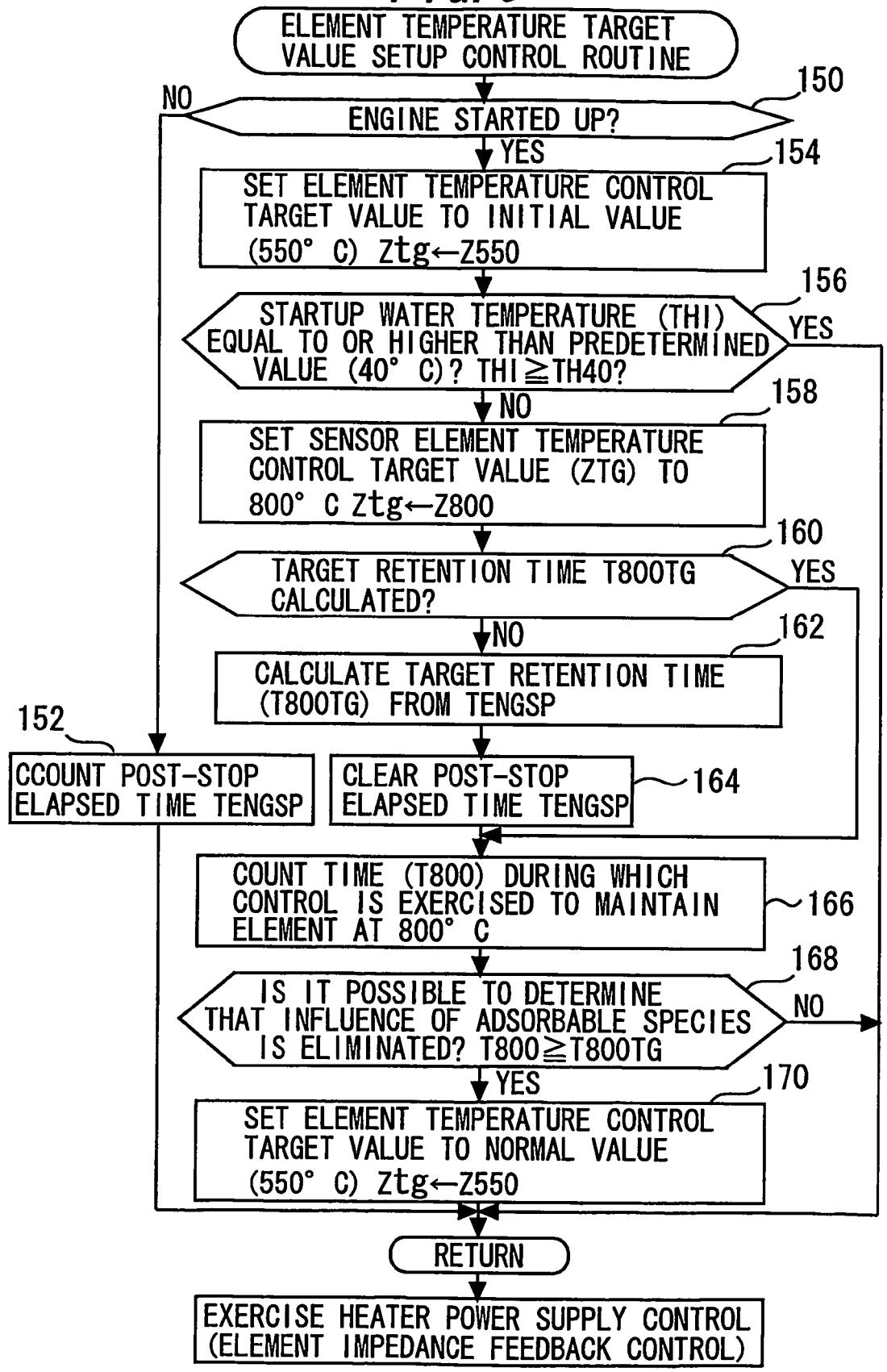
FIG. 9 is a flowchart illustrating a routine that is executed by a third embodiment of the present invention.

FIG. 9 is a flowchart illustrating a routine that the microcomputer 30 performs to implement the above functionality. In the routine shown in FIG. 9, step 150 is first performed to determine whether the internal combustion engine is started up. If the determination result does not indicate that the internal combustion engine is started up, step 152 is performed to count the elapsed time TENGSP from an internal combustion engine stop. The present embodiment assumes that the elapsed time TENGSP can be counted while the internal combustion engine is stopped.

If, on the other hand, the determination result obtained in step 150 indicates that the internal combustion engine is started up, step 154 is performed to set an initial value (e.g., 550° C. ) as a target temperature for the sensor element 14. Next, step 156 is performed to determine whether a startup water temperature THI is equal to or higher than a determination temperature TH40. If the determination of THI≧TH40 is negative, the target temperature for the sensor element 14 is changed to a high-temperature target value (e.g., 800° C.) (step 158). These processing steps are the same as steps 132 through 136 in FIG. 8.

Next, the routine shown in FIG. 9 performs step 160 to determine whether the target time (hereinafter referred to as the "target retention time T800TG") during which the sensor element 14 should be maintained at a high-temperature target value of 800° C. is already calculated. If the obtained determination result indicates that the target retention time T800TG is calculated, the program flow skips processing steps 162 and 164, which will be described later.

If, on the other hand, the obtained determination result does not indicate that the target retention time T800TG is calculated, step 162 is performed to calculate the target retention time T800TG in accordance with the elapsed time TENGSP after an internal combustion engine stop. The target retention time T800TG (that is, the duration of high-temperature control) should coincide with the time required for adsorbable species desorption. Therefore, it is required that the target retention time T800TG increase with an increase in the amount of adsorbable species adsorption, that is, with an increase in the elapsed time TENGSP after an internal combustion engine stop. To meet the above requirement in the present embodiment, the microcomputer 30 stores a map that defines the relationship between the elapsed time TENGSP and the target retention time T800TG. In step 162, the map is referenced to set the value T800TG that corresponds to the elapsed time TENGSP. As a result, the longer the elapsed time TENGSP after an internal combustion engine stop, the longer the target retention time T800TG is set.

Next, the routine shown in FIG. 9 performs step 164 to clear the elapsed time TENGSP after an internal combustion engine stop. In the subsequent processing cycles, the target retention time T800TG is maintained equal to the value calculated in the present processing cycle because the steps 162 and 164 are skipped in those cycles.

After completion of the above processing steps, step 166 is performed to count the length of time during which control is exercised to maintain the sensor element 14 at a temperature of 800° C. (the time during which Ztg=Z800 or the time elapse after an element temperature of 800° C. is reached; hereinafter referred to as the "high-temperature control time T800"). Next, step 168 is performed to determine whether the high-temperature control time T800 is equal to or longer than the target retention time T800TG.

If the obtained determination result denies T800≧T800TG, it can be concluded that adsorbable species desorption from the sensor element 14 is not completed. In such an instance, the current routine terminates while the ensuing target impedance Ztg is maintained at Z800, and high-temperature control is continuously exercised over the sensor element 14.

If, on the other hand, the determination result obtained in step 168 indicates that T800≧T800TG, it can be concluded that adsorbable species desorption from the sensor element 14 is completed. In this instance, the target temperature for impedance feedback control is changed to a normal value (550° C.) (step 170). As a result, high-temperature control terminates and then normal impedance feedback control starts.

When the process described above is performed, high-temperature control is exercised after internal combustion engine startup so as to promote adsorbable species desorption and reduce the period of time during which the sensor output suffers rich displacement. Further, the process causes the target retention time T800 to increase with an increase in the elapsed time TENGSP between an internal combustion engine stop and a restart, and ensures that the completion of adsorbable species desorption precisely coincides with the end of high-temperature control. As a result, the controller according to the present embodiment minimizes the influence of oxygen sensor output deviation, which is caused by the adsorbable species, and begins to properly detect the exhaust gas status immediately after internal combustion engine startup without extra power consumption and without causing avoidable damage to the sensor element 14.

[Modifications of and Supplementary Information About the Third Embodiment]

The third embodiment, which is described above, checks whether the target retention time T800TG is reached by the high-temperature control time T800 in order to determine whether adsorbable species desorption is completed. However, an alternative determination method may be used. For example, the above determination may be formulated, as is the case with the second embodiment, by checking whether the recovery determination value GAsumTG is reached by the cumulative intake air amount GAsum (the value GAsumTG is set according to the value TENGSP in this instance).

Further, the third embodiment, which is described above, ensures that the longer the elapsed time after an internal combustion engine stop, the longer the target retention time T800TG. In this manner, the third embodiment varies the duration of high-temperature control in accordance with the influence of the amount of adsorbable species adsorption. However, an alternative method may be used. More specifically, the rate of increase in the high-temperature control time T800 may be reduced with an increase in the elapsed time TENGSP after an internal combustion engine stop so that the duration of high-temperature control is varied in accordance with the influence of the amount of adsorbable species adsorption.

Furthermore, the third embodiment, which is described above, does not vary the duration of high-temperature control in accordance with the lean time that arises after internal combustion engine startup. However, the present invention is not limited to such a scheme. More specifically, the controller according to the third embodiment may cause the duration of high-temperature control to decrease with an increase in the lean time after internal combustion engine startup, as is the case with the second embodiment.

In the third embodiment, which is described above, the high-temperature control time T800 corresponds to a "characteristics recovery value" according to the fifth aspect of the present invention, and the target retention time T800TG corresponds to a "recovery determination value" according to the fifth aspect of the present invention. "Recovery value counting unit" according to the fifth aspect of the present invention is implemented when the microcomputer 30 performs processing step 166. Further, "heater control unit" according to the fifth aspect of the present invention is implemented when the microcomputer 30 performs processing steps 158 and 168. "Stop time counting unit" according to the fifth aspect of the present invention is implemented when the microcomputer 30 performs processing step 152. "Determination value correction unit" according to the fifth aspect of the present invention is implemented when the microcomputer 30 performs processing step 162.

Fourth Embodiment

[Features of the Fourth Embodiment]

The fourth embodiment of the present invention will now be described with reference to FIG. 10. The controller according to the fourth embodiment is implemented when the hardware configuration shown in FIG. 1 or 2 is employed to let the microcomputer 30 execute a routine shown in FIG. 10 in place of or together with the routine shown in FIG. 5 or 7.

As described earlier, the desorption of the adsorbable species adsorbed by the sensor element 14 remarkably progresses in a lean atmosphere. Therefore, whether or not the desorption of the adsorbable species is completed can also be accurately determined by judging whether an adequate lean time is generated after internal combustion engine startup. Therefore, the present embodiment checks the cumulative lean time generated after internal combustion engine startup to determine the time at which high-temperature control over the sensor element 14 should terminate.

[Process Performed by the Fourth Embodiment]

Figure 10:
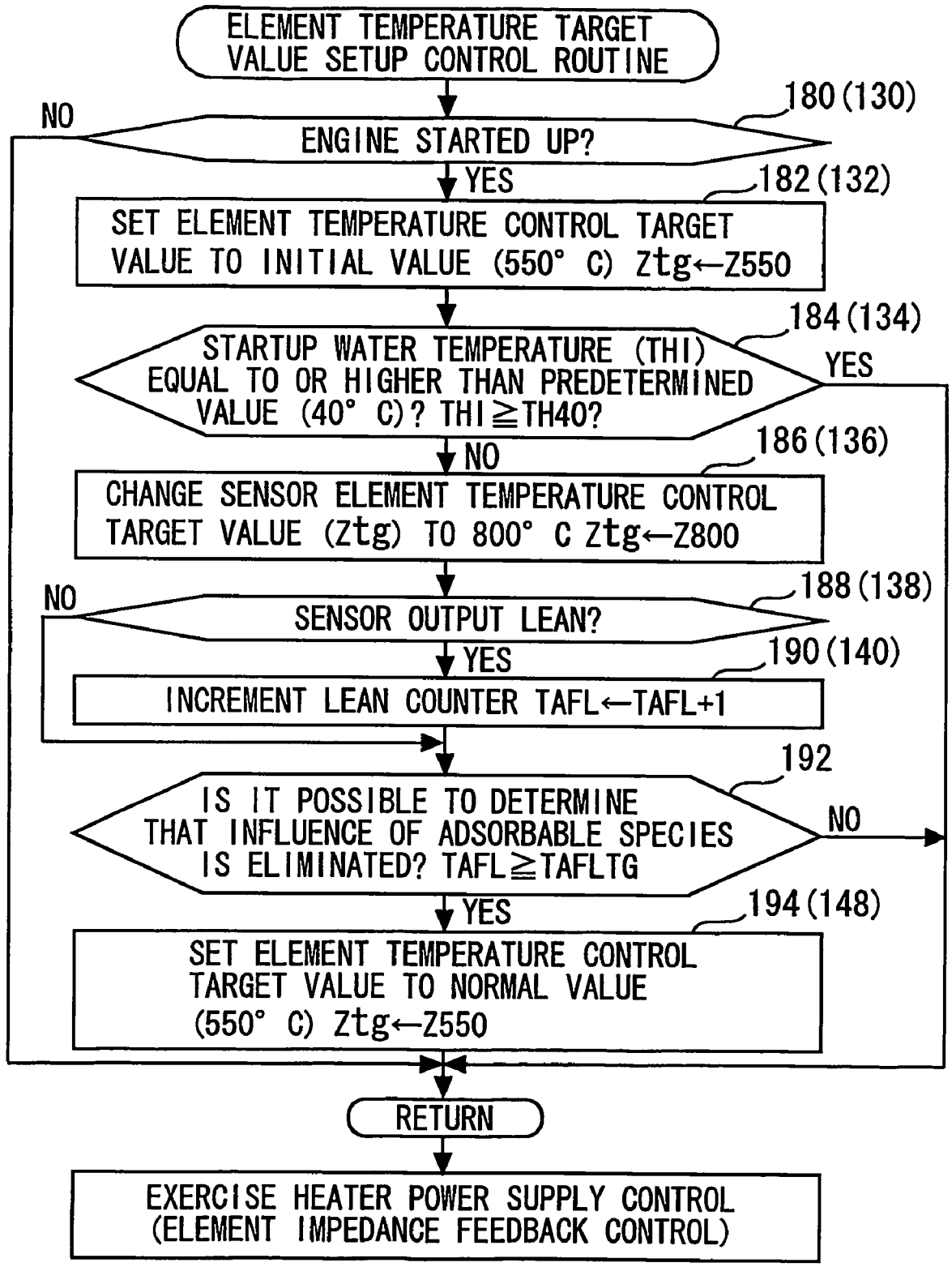
FIG. 10 is a flowchart illustrating a routine that is executed by a fourth embodiment of the present invention.

FIG. 10 is a flowchart illustrating a routine that the microcomputer 30 performs to implement the above functionality. In the routine shown in FIG. 10, processing steps 180 through 190 are the same as processing steps 130 through 140 in FIG. 8. Processing step 194 in FIG. 10 is also the same as processing step 148 in FIG. 8. As regards the steps in FIG. 10 that are the same as the steps in FIG. 8, their description is omitted or abridged to avoid a redundant description.

When the necessity for high-temperature control is recognized after internal combustion engine startup (step 184), the routine shown in FIG. 10 sets a high-temperature target value (800° C.) as the target temperature for the sensor element 14 (step 186). Next, the cumulative value TAFL of the time during which the exhaust air-fuel ratio is lean is counted in accordance with the output of the oxygen sensor 10 (step 190). The above process is also performed by the routine shown in FIG. 8.

Next, the routine shown in FIG. 10 determines whether the counted cumulative value TAFL of the lean time is equal to or larger than the recovery determination value TAFLTG (step 192). The microcomputer 30 stores the recovery determination value TAFLTG, which is to be compared against the cumulative lean time TAFL. The lean time that is required for the adsorbable species adsorbed by the sensor element 14 to become thoroughly desorbed after internal combustion engine startup is set as the recovery determination value TAFLTG.

Therefore, if the determination result obtained in step 192 does not indicate that TAFL≧TAFLTG, it can concluded that the completion of adsorbable species desorption is not recognized. In this instance, the current routine terminates while the ensuing target impedance Ztg is maintained at Z800, and high-temperature control is continuously exercised over the sensor element 14.

If, on the other hand, the determination result obtained in step 192 indicates that TAFL≧TAFLTG, it can be concluded that adsorbable species desorption is completed. In this instance, the target temperature for impedance feedback control is changed to a normal value (550° C.) (step 194). As a result, high-temperature control terminates and then normal impedance feedback control starts.

When the process described above is performed, high-temperature control is exercised after internal combustion engine startup so as to promote adsorbable species desorption and reduce the period of time during which the sensor output suffers rich displacement. Further, the process determines the time of high-temperature control termination by paying attention to the cumulative lean time. Therefore, performing a relatively simple process makes it possible to ensure that the completion of adsorbable species desorption precisely coincides with the end of high-temperature control. As a result, the controller according to the present embodiment minimizes the influence of oxygen sensor output deviation, which is caused by the adsorbable species, and begins to properly detect the exhaust gas status immediately after internal combustion engine startup without extra power consumption and without causing avoidable damage to the sensor element 14.

[Modifications of and Supplementary Information About the Fourth Embodiment]

The fourth embodiment, which is described above, determines the time in which the high-temperature control is performed in accordance with the cumulative lean time TAFL only. Alternatively, however, the time for the high-temperature control may be varied in accordance, for instance, with the cumulative intake air amount GAsum that has been counted since internal combustion engine startup, the high-temperature control time T800 for the sensor element 14, or the elapsed time TENGSP after an internal combustion engine stop. More specifically, the fourth embodiment may decrease the recovery determination value TAFLTG, which is considered to a fixed value, with an increase in the value GAsum, decrease the recovery determination value TAFLTG with an increase in the value T800, and increase the recovery determination value TAFLTG with an increase in the value TENGSP. Alternatively; the fourth embodiment may increase the rate of the increase in the cumulative value TAFL, which is considered to be fixed, with an increase in the value GAsum, increase the rate of the increase in the cumulative value TAFL with an increase in the value T800, and decrease the rate of the increase in the cumulative value TAFL with an increase in the value TENGSP.

In the fourth embodiment, which is described above, "cumulative lean time counting unit" according to the sixth aspect of the present invention is implemented when the microcomputer 30 performs processing steps 188 and 190, and "heater control unit" according to the sixth aspect of the present invention is implemented when the microcomputer 30 performs processing steps 186 and 192. Further, "recovery value counting unit" according to the seventh aspect of the present invention is implemented when the microcomputer 30 counts the elapsed time after internal combustion engine startup or the cumulative intake air amount, and "determination value correction unit" according to the seventh aspect of the present invention is implemented when the microcomputer 30 corrects the tendency of the increase in the recovery determination value TAFLTG or cumulative value TAFL in accordance with the above count. Furthermore, "stop time counting unit" according to the eighth aspect of the present invention is implemented when the microcomputer 30 counts the elapsed time after an internal combustion engine stop, and "determination value correction unit" according to the eighth aspect of the present invention is implemented when the microcomputer 30 corrects the tendency of the increase in the recovery determination value TAFLTG or cumulative value TAFL in accordance with the above count.

Fifth Embodiment

[Features of the Fifth Embodiment]

The fifth embodiment of the present invention will now be described with reference to FIGS. 11 and 12. The controller according to the fifth embodiment is implemented when the hardware configuration shown in FIG. 1 or 2 is employed to let the microcomputer 30 execute a routine shown in FIG. 11 in place of or together with the routine shown in FIG. 5 or 7.

As described earlier, the output of the oxygen sensor 10 suffers temporary sensor output rich displacement immediately after internal combustion engine startup due to the influence of the adsorbable species. It is difficult to completely avoid adsorbable species adsorption. Therefore, it is also difficult to avoid sensor output rich displacement. There is a correlation between sensor output rich displacement and adsorbable species desorption amount. Further, the amount of adsorbable species desorption greatly correlates with the amount of adsorbable species adsorption prevailing at the beginning of desorption, that is, the initial amount of adsorbable species adsorption, and the subsequent elapsed time.

Therefore, the amount of adsorbable species desorption can be roughly estimated from the initial adsorption amount and the elapsed time after the beginning of desorption. When the amount of desorption is estimated, it is possible to estimate the amount of sensor output rich displacement, which is caused by the adsorbable species. When the amount of sensor output rich displacement is estimated, it is possible to correct the output of the oxygen sensor 10. Thus, the status of the exhaust gas can be accurately detected even while rich displacement is encountered. Under these circumstances, the present embodiment calculates the amount of rich displacement superposed over the sensor output in accordance with the amount of adsorbable species adsorbed at internal combustion engine startup and the elapsed time after the beginning of desorption, and corrects the output of the oxygen sensor 10 by using the calculated displacement amount as a correction value after internal combustion engine startup.

[Process Performed by the Fifth Embodiment]

Figure 11:
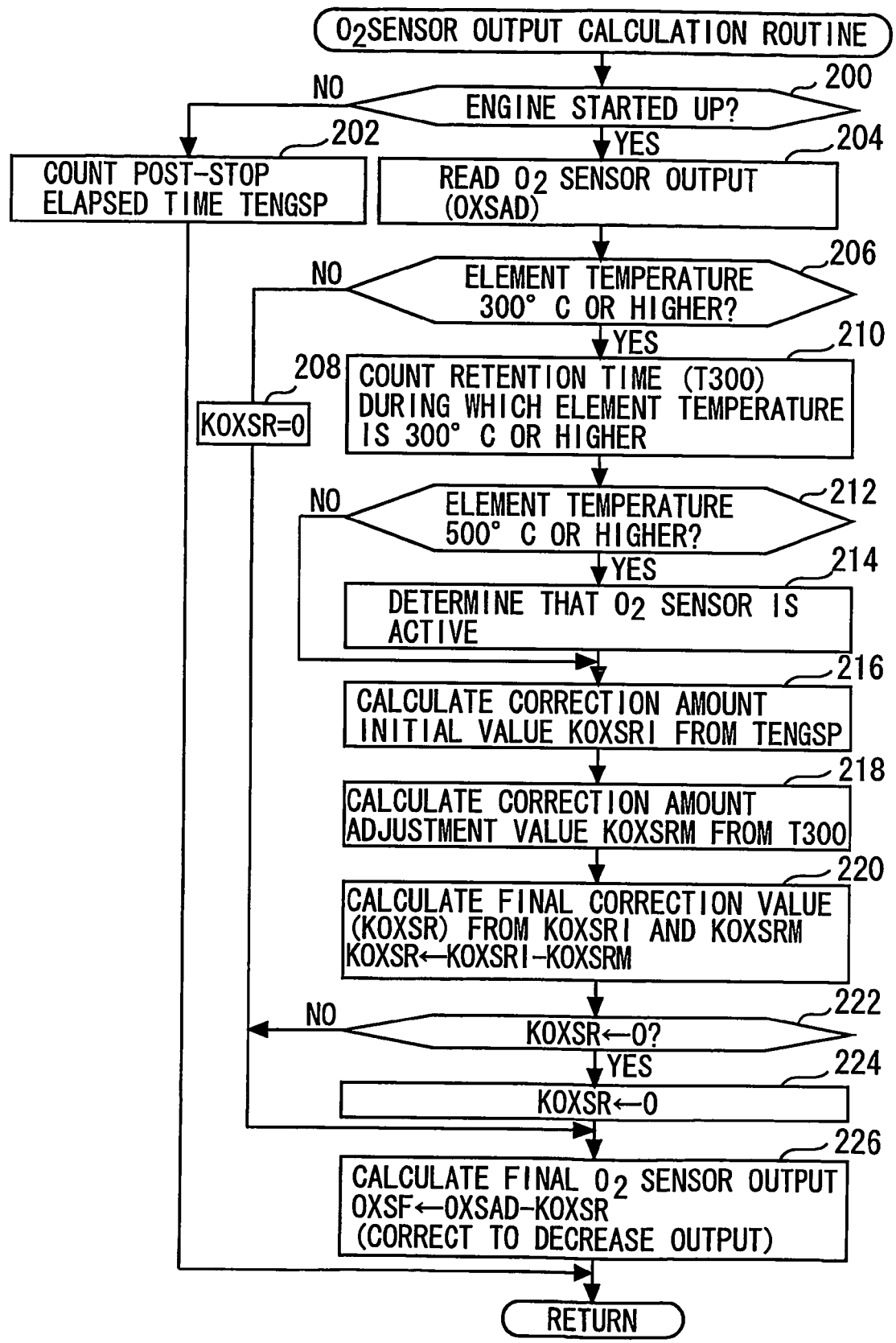
FIG. 11 is a flowchart illustrating a routine that is executed by a fifth embodiment of the present invention.

FIG. 11 is a flowchart illustrating a routine that the microcomputer 30 performs to implement the above functionality. In the routine shown in FIG. 11, step 200 is first performed to determine whether the internal combustion engine is started up. If the obtained determination result does not indicate that the internal combustion engine is started up, step 202 is performed to count the elapsed time TENGSP after an internal combustion engine stop. The present embodiment assumes that the microcomputer 30 can count the elapsed time TENGSP while the internal combustion engine is stopped.

If the determination result obtained in step 200 indicates that the internal combustion engine is started up, step 204 is performed to read the sensor output OXSAD of the oxygen sensor 10. Next, step 206 is performed to determine whether the temperature of the sensor element 14 is equal to or higher than 300° C., that is, whether the temperature for the start of adsorbable species desorption is reached.

If the determination result obtained in step 206 indicates that the element temperature is lower than 300° C., it can be concluded that sensor output rich displacement, which is caused by the adsorbable species, is not encountered yet. In this instance, step 208 is performed to set a final correction value KOXSR to zero. Next, step 226 is followed to perform a process for calculating the final sensor output as described later.

If, on the other hand, the determination result obtained in step 206 indicates that the element temperature is equal to or higher than 300° C., it can be concluded that rich displacement, which is caused by the adsorbable species, is encountered. In this instance, step 210 is performed to count the elapsed time after an element temperature of 300° C. or higher is reached, that is, the elapsed time after the start of adsorbable species desorption, as the "300° C. retention time T300".

Next, the routine shown in FIG. 11 performs step 212 to determine whether a normal target temperature of 550° C. is reached by the element. If the determination result indicates that the element temperature is equal to or higher than 550° C., step 214 is performed to determine that the oxygen sensor 10 is active.

After completion of the above processing steps, step 216 is performed to calculate a correction amount initial value KOXSRI in accordance with the elapsed time TENGSP, which is calculated while the internal combustion engine is stopped. The correction amount initial value KOXSRI is a value for correcting the amount of rich displacement that is encountered at the beginning of adsorbable species desorption. This value KOXSRI should increase with an increase in the amount of initial adsorption. Therefore, the value KOXSRI should increase with an increase in the elapsed time TENGSP after an internal combustion engine stop.

Figures 12A, 12B, 12C:
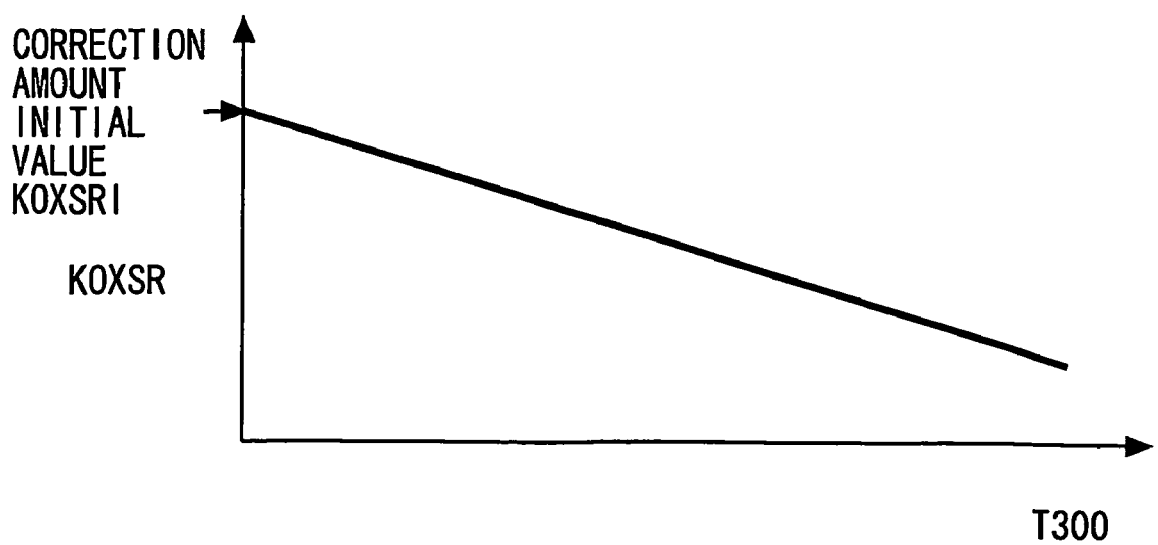
FIGS. 12A and 12B show examples of a map that is referenced when the routine shown in FIG. 11 is executed.
FIG. 12C illustrates how a final correction value calculated by the routine shown in FIG. 11 changes with time.

FIG. 12A shows an example of a map that the microcomputer 30 references to calculate the correction amount initial value KOXSRI in step 216. This map is created to provide consistency with the amount of initial adsorption so that the correction amount initial value KOXSRI increases with an increase in the after-stop elapsed time TENGSP. According to processing step 216, a value accurately consistent with the amount of rich displacement encountered at the beginning of desorption can be set as the correction amount initial value KOXSRI.

Next, the routine shown in FIG. 11 performs step 218 to calculate a correction amount adjustment value KOXSRM in accordance with the 300° C. retention time T300. The amount of sensor output rich displacement decreases as adsorbable species desorption progresses. Therefore, the amount of rich displacement gradually decreases with an increase in the 300° C. retention time T300. The correction amount adjustment value KOXSRM, which is calculated in step 218, corresponds to the above-mentioned change in the amount of rich displacement.

FIG. 12B shows an example of a map that the microcomputer 30 references to calculate the correction amount adjustment value KOXSRM in step 218. This map is created to provide consistency with a change in the amount of rich displacement so that the correction amount adjustment value KOXSRM increases with an increase in the 300° C. retention time T300. According to processing step 218, therefore, a value accurately consistent with the amount of rich displacement reduction encountered after the beginning of desorption can be set as the correction amount adjustment value KOXSRM.

When the correction amount initial value KOXSRI and correction amount adjustment value KOXSRM are calculated as described above, the final correction value KOXSR is calculated by the following equation (step 220):

$$KOXSR = KOXSRI - KOXSRM \quad (1)$$

FIG. 12C illustrates how the final correction value KOXSR, which is calculated from Equation (1) above, changes with time. Since the correction amount adjustment value KOXSRM increases with an increase in the 300° C. retention time, the final correction value KOXSR gradually decreases with an increase in the 300° C. retention time with the correction amount initial value KOXSRI applied as the maximum value as indicated in FIG. 12C. The changes in the final correction value KOXSR precisely correspond to the amount of sensor output rich displacement, which is caused by adsorbable species desorption.

Next, the routine shown in FIG. 11 performs a guard process to ensure that the lower-limit value for the final correction value KOXSR is zero (0) (steps 222 and 224). The output OXSAD of the oxygen sensor 10 and the final correction value KOXSR are then substituted into the following equation to calculate a final oxygen sensor output OXSF (step 226):

$$OXSF = OXSAD - KOXSR \quad (2)$$

When the process described above is performed, the final correction value KOXSR that is accurately consistent with the degree of rich displacement can be calculated after adsorbable species desorption begins following to the internal combustion engine starts up. When the calculated final correction value KOXSR is then used to correct the sensor output OXSAD, it is possible to calculate the final oxygen sensor output OXSF from which the influence of rich displacement is eliminated. As a result, the controller according to the present embodiment minimizes the influence of oxygen sensor output deviation, which is caused by the adsorbable species, and begins to properly detect the exhaust gas status immediately after internal combustion engine startup.

The fifth embodiment, which is described above, assumes that the degree of rich displacement decreases with an increase in the 300° C. retention time T300, and determines the correction amount adjustment value KOXSRM as a function of T300. However, an alternative method may be used to determine the correction amount adjustment value KOXSRM. More specifically, the correction amount adjustment value KOXSRM may be determined as a function, for instance, of the cumulative intake air amount GA prevailing after an element temperature of 300° C. is exceeded or the lean time prevailing after an element temperature of 300° C. is exceeded.

In the fifth embodiment, which is described above, the 300° C. retention time T300 corresponds to a "desorption progress value" according to the ninth aspect of the present invention and the final correction value KOXSR corresponds to a "sensor output correction value" according to the ninth aspect of the present invention. Further, the fifth embodiment implements "element temperature acquisition unit" according to the ninth aspect of the present invention when the microcomputer 30 detects the temperature of the sensor element 14 for impedance feedback control, "desorption progress value counting unit" according to the ninth aspect of the present invention when the microcomputer 30 performs processing step 210, "output correction unit" according to the ninth aspect of the present invention when the microcomputer 30 performs processing step 226, and "correction value calculation unit" according to the ninth aspect of the present invention when the microcomputer 30 performs processing step 218 and 220. Furthermore, the fifth embodiment implements "stop time counting unit" according to the tenth aspect of the present invention when the microcomputer 30 performs processing step 202 and "initial value setup unit" according to the tenth aspect of the present invention when the microcomputer 30 performs processing step 216.

The invention claimed is:

1. An exhaust sensor control system for an exhaust sensor mounted in an exhaust path of an internal combustion engine, wherein said exhaust sensor includes a sensor element for generating an output in accordance with the status of an exhaust gas and a heater for heating said sensor element, the exhaust sensor control system comprising:
    heater control means for continuing power supply control over said heater until the exhaust gas temperature at the exhaust sensor drops below 80° C. after the internal combustion engine is stopped.

2. The exhaust sensor control system according to claim 1, further comprising element temperature acquisition means for acquiring the temperature of said sensor element, wherein said heater control means includes after-stop power supply control means for controlling said heater with a predetermined temperature between 300° C. and 500° C. set as a target temperature for said sensor element after the internal combustion engine is stopped.

3. The exhaust sensor control system according to claim 1, wherein said heater control means comprises
    stop moment exhaust temperature estimation means, which estimates the exhaust path temperature at a stop moment of the internal combustion engine, and
    temperature condition determination means, which determines whether the exhaust path temperature is below 80° C. based on the exhaust path temperature at said stop moment and the elapsed time after said internal combustion engine is stopped.

* * * * *